United States Patent [19]
Tu et al.

[11] Patent Number: 5,783,679
[45] Date of Patent: Jul. 21, 1998

[54] PURINE NUCLEOSIDE MODIFICATIONS BY PALLADIUM CATALYZED METHODS AND OLIGONUCLEOTIDES CONTAINING SAME

[75] Inventors: Chi Tu, Louisville; Bruce Eaton, Boulder, both of Colo.

[73] Assignee: NeXstar Pharmaceuticals, Inc., Boulder, Colo.

[21] Appl. No.: 441,881

[22] Filed: May 16, 1995

Related U.S. Application Data

[63] Continuation of Ser. No. 347,600, Dec. 1, 1994, Pat. No. 5,580,972, which is a continuation-in-part of Ser. No. 76,735, Jun. 14, 1993, Pat. No. 5,428,149.

[51] Int. Cl.$^6$ .................... C07H 19/16; C07H 21/00
[52] U.S. Cl. .................. 536/23.1; 536/27.14; 536/27.21; 536/27.6; 536/27.81
[58] Field of Search .................. 536/26.7, 26.71, 536/26.72, 27.14, 27.6, 27.81, 23.1, 27.21; 514/45, 46, 47, 48, 43

[56] References Cited

U.S. PATENT DOCUMENTS

| | | | |
|---|---|---|---|
| 5,047,519 | 9/1991 | Hobbs, Jr. et al. | 536/27.14 |
| 5,053,499 | 10/1991 | Kojima et al. | 536/27.14 |
| 5,428,149 | 6/1995 | Eaton | 536/28.55 |

FOREIGN PATENT DOCUMENTS

| | | |
|---|---|---|
| WO 90/15065 | 12/1990 | WIPO. |
| WO 91/06556 | 5/1991 | WIPO. |
| WO 91/06629 | 5/1991 | WIPO. |
| WO 91/10671 | 7/1991 | WIPO. |
| WO 91/14696 | 10/1991 | WIPO. |

OTHER PUBLICATIONS

Hung et al., J. Org. Chem., vol. 47, No. 3, pp. 448–453, (1982).
Van Aerschot et al., J. Med. Chem., vol. 36, No. 20, pp. 2938–2942, (1993).
Sagi et al., J. Med. Chem., vol. 37, No. 9, pp. 1307–1311, (1994).
Crisp et al., Tetrahedron Letters, vol. 31, No. 9, pp. 1347–1350 (1990).
Chemical Abstracts, vol. 115, No. 9, Sentemov et al., Abstract No.: 92415h.
Arai and Daves, Jr. (1978) J. Am. Chem. Soc. 100:287.
Bergstrom et al. (1981) J. Org. Chem. 46:1432.
Bergstrom and Ruth (1976) J. Am. Chem. Soc. 98:1587.
Bergstrom et al. (1982) J. Org. Chem. 47:2174.
Crisp (1989) Syn. Commun. 19:2117.
Dreyer and Dervan (1985) Proc. Natl. Acad. Sci. USA 82:968.
Guschlbauer et al. (1977) Nucleic Acids Res. 4:1933.
Hobbs et al. (1973) Biochemistry 12:5138.
Hacksell and Daves, Jr. (1983) J. Org. Chem. 48:2870.
Ikehara and Tada (1968) in *Synthetic Procedures in Nucleic Acid Chemistry*, Zorbach, W.W.; Tipson, R.S. Eds.; John Wiley and Sons, NY; p. 189.
Pieken et al. (1991) Science 253:314.
Ruth and Bergstrom (1978) J. Org. Chem. 43:2870.
Sagi et al. (1994) J. Med. Chem. 37:1307.
Sessler et al. (1993) J. Am. Chem. Soc. 115:10418.
Shibahara et al. (1987) Nucliec Acids Res. 15:4403.
Sproat et al. (1989) Nucleic Acids Res. 17:3373.
Tronchet et al. (1988) Nucleosides & Nucleotides, 7:249.
Tuerk and Gold (1990) Science 249:505.
Van Aerschot et al. (1993) J. Med. Chem. 36:2938.

*Primary Examiner*—James O. Wilson
*Attorney, Agent, or Firm*—Swanson & Bratschun LLC

[57] ABSTRACT

This invention discloses an improved method for the preparation modified purine nucleosides at the 2-, 6- or 8-position of the purine ring, using a palladium catalyst.

7 Claims, No Drawings

PURINE NUCLEOSIDE MODIFICATIONS BY PALLADIUM CATALYZED METHODS AND OLIGONUCLEOTIDES CONTAINING SAME

This application is a continuation of U.S. patent application Ser. No. 08/347,600, filed Dec. 1, 1994, now U.S. Pat. No. 5,580,972, which is a continuation-in-part of U.S. patent application Ser. No. 08/076,735, filed Jun. 14, 1993, now U.S. Pat. No. 5,428,149.

FIELD OF THE INVENTION

This invention relates to the field of nucleic acid chemistry, specifically to a process for preparing modified purines. The purine compounds of the invention have been modified at the 2-, 6- or 8-position of the purine ring. Most preferably, the invention includes a process for preparing 8-position modified purine compounds. The present invention also includes the modified purines produced by the method.

BACKGROUND OF THE INVENTION

Until quite recently, the consideration of oligonucleotides in any function other than strictly informational was unheard of. Despite the fact that certain oligonucleotides were known to have interesting structural possibilities (e.g., t-RNAs) and other oligonucleotides were bound specifically by polypeptides in nature, very little attention had been focussed on the non-informational capacities of oligonucleotides. For this reason, among others, little consideration had been given to using oligonucleotides as pharmaceutical compounds.

There are currently at least three areas of exploration that have led to serious studies regarding the use of oligonucleotides as pharmaceuticals. In the most advanced of the fields, antisense oligonucleotides are utilized to bind to certain coding regions in an organism to prevent the expression of proteins or to block various cell functions. The discovery of RNA species with catalytic functions—ribozymes—has led to the consideration of RNA species that serve to perform intracellular reactions that will achieve desired effects. And lastly, the discovery of the SELEX process (Systematic Evolution of Ligands by EXponential Enrichment) has shown the research community that oligonucleotides can be identified that will bind to almost any biologically interesting target.

The use of antisense oligonucleotides as a method for controlling gene expression and the potential for using oligonucleotides as pharmaceutical materials has prompted investigations into the introduction of a number of chemical modifications into oligonucleotides to increase their therapeutic activity. Such modifications are designed to increase cell penetration of the oligonucleotides, to stabilize them from nucleases and other enzymes that degrade or interfere with the structure or activity of the oligonucleotide analogs in the body, to enhance their binding to targeted nucleic acids, to provide a mode of disruption (terminating event) once sequence-specifically bound to targeted nucleic acids, and to improve their pharmacokinetic properties. For example, PCT Patent Application Publication WO 91/14696, entitled: Oligonucleotide-Transport Agent Disulfide Conjugates, describes a method for chemically modifying antisense oligonucleotides to enhance entry into a cell.

A variety of methods have been used to render oligonucleotides resistant to degradation by exonucleases. PCT Patent Application Publication WO 90/15065, entitled: Exonuclease-Resistant Oligonucleotides and Methods for Preparing the Same, describes a method for making exonuclease-resistant oligonucleotides by incorporating two or more phosphoramidite and phosphoromonothionate and/or phosphorodithionate linkages at the 5' and/or 3' ends of the oligonucleotide. PCT Patent Application Publication WO 91/06629, entitled: Oligonucleotide Analogs with Novel Linkages, describes oligonucleotide compounds with one or more phosphodiester linkages between adjacent nucleotides replaced by a formacetal/ketal type linkage which are capable of binding RNA or DNA.

A common strategy for stabilization of RNA against endonucleolytic cleavage is to modify the 2'-position of ribonucleotides. Interference with base recognition by enzymes can be used to approach stabilization against base-specific endonucleolytic cleavage. Several strategies for this modification are known, including modification with 2'-amino and 2'-fluoro (Hobbs et al. (1973) Biochemistry 12:5138; Guschlbauer et al. (1977) Nucleic Acids Res. 4:1933), and 2'-OCH$_3$ (Shibahara et al. (1987) 15:4403; Sproat et al. (1989) Nucleic Acids Res. 17:3373). PCT Patent Application Publication WO 91/06556, entitled: 2' Modified Oligonucleotides, describes nuclease-resistant oligomers with substituents at the 2' position. PCT Patent Application Publication WO 91/10671, entitled:

Compositions and Methods for Detecting and Modulating RNA Activity and Gene Expression, describes antisense oligonucleotides chemically modified at the 2' position and containing a reactive portion capable of catalyzing, alkylating, or otherwise effecting the cleavage of RNA, a targeting portion, and a tether portion for connecting the targeting and reactive portions.

The 5-position of pyrimidines may also be chemically modified. The introduction of modifications at the C-5 position of pyrimidines may be envisioned to interfere with the recognition by pyrimidine specific endonucleases. However, this concept is not as clear cut as the modification of the 2'-position of ribonucleotides.

The use of palladium to catalyze carbon-carbon bond formation at the 5 position of pyrimidine nucleosides is known. A superior method for 5-position modification of pyrimidines is described in U.S. Ser. No. 08/076,735, entitled "Method for Palladium Catalyzed Carbon-Carbon Coupling and Product," which is herein incorporated by reference in its entirety. The first examples of 5-position pyrimidine modifications were demonstrated by Bergstrom (Bergstrom et al. (1976) J. Am. Chem. Soc. 98:1587, (1978) J. Org. Chem. 43:2870, (1981) J. Org. Chem. 46:1432 and 2870, (1982) J. Org. Chem. 47:2174) and Daves (Arai and Daves (1978) J. Am. Chem. Soc., 100:287; Lee and Daves (1983) J. Org. Chem. 48:2870). Bergstrom and Daves used 5-mercurial-deoxyuridine compounds, the same as those used by Dreyer and Dervan ((1985) Proc. Natl. Acad. Sci. USA 82:968), to tether functional groups to oligonucleotides.

One method for simple carbon-carbon coupling reactions to the 5-position of uridines is described in the work of Crisp (1989) Syn. Commun. 19:2117. Crisp forms deoxyuridines functionalized at the 5 position by reacting protected 5-iodo-2'-deoxyuridine with alkenylstannanes in acetonitrile in the presence of a Pd (II) catalyst.

To date, very little work has been done to modify purine nucleosides using palladium catalysis. Aeroschot et al., ((1993) J. Med. Chem 36:2938–2942) report that 2-, 6-, and 8-halogenated adenosines can be modified with symmetric organotin reagents. However, symmetric organotin compounds are not widely available. Sessler et al., ((1993) J. Am. Chem. 115:10418–10419) describe the arylation of protected 8-bromoguanosine with 4-tributyltinbenzaldehyde. However, using this procedure, a significant amount of starting material (28%) was unreacted.

SELEX (Systematic Evolution of Ligands for EXponential Enrichment) is a method for identifying and producing nucleic acid ligands, termed "nucleic acid antibodies", e.g., nucleic acids that selectively bind to target molecules (Tuerk and Gold (1990) Science 249:505). The method involves selection from a mixture of candidates and step-wise iterations of structural improvement, using the same general selection theme, to achieve virtually any desired criterion of affinity and selectivity. Starting from a mixture of nucleic acids, the method includes steps of contacting the mixture with the target under conditions favorable for interaction, partitioning non-interacting nucleic acids from those nucleic acids which have interacted with the target molecules, dissociating the nucleic acid-target pairs, amplifying the nucleic acids dissociated from the nucleic acid-target pairs to yield a mixture of nucleic acids enriched for those which interact with the target, then reiterating the steps of interacting, partitioning, dissociating and amplifying through as many cycles as desired.

The methods of the present invention may be combined with SELEX to produce nucleic acids containing modified nucleotides. The presence of modified nucleotides may result in nucleic acids with an altered structure exhibiting an increased capacity to interact with target molecules. The steric and electronic influence of modified purines may also act to prevent nuclease degradation. Without wishing to be bound by any theory, it is believed that the preferred modification is an attachment at the 8-position of the purine ring so that the modification is presented to the major groove of duplex regions.

BRIEF SUMMARY OF THE INVENTION

The present invention includes a novel method for introducing chemical moieties at various positions of the purine ring utilizing a palladium catalyst. Preferably, the modifications are at the 2-, 6-, or 8-positions of the purine ring, most preferably at the 8-position. Particularly preferred modifications of the purine ring include introduction of alkyl, alkenyl or aryl groups.

This invention includes a reaction scheme for producing a wide variety of modified purine molecules. A key element in the production of the modified purines is the use of a palladium catalyst. The improved $PdL_3$ catalysts of the present invention act to accelerate the formation of products that in some cases could not be formed or could be formed only slowly and in low yields utilizing the catalysts of the prior art.

More specifically, the invention provides a method for the preparation of a modified purine comprising the steps of reacting a purine starting material containing a leaving group attached to a carbon atom of the purine starting material with an organotin compound in the presence of a $PdL_3$ catalyst; and isolating the modified purine. The modified purines produced by this method are also included.

This invention further includes a method of preparing stabilized nucleic acids wherein the modified purine is coupled to a sugar modified at the 2'-position.

DETAILED DESCRIPTION OF THE INVENTION

The present invention includes a method for modifying a purine ring via a palladium catalyst. A purine has the following structure and conventional numbering:

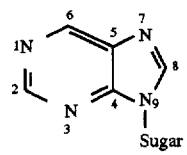

The purine ring can be modified at positions 2-, 6- and 8- of the purine ring; most preferably the 8-position is modified. Introduction of a variety of modifications to the purine ring are contemplated by this invention. However, particularly preferred modifications to the purine ring include introduction of alkyl, alkenyl or aryl groups.

The present invention extends to all novel compounds that can be prepared according to the methods of the present invention. The only known modified purines are 8-phenyl adenosine and 8-vinyl adenosine. All other modified purines are novel. The present invention also includes oligonucleotides that contain one or more of the novel substituted purines of this invention.

The general reactions of the present invention can be characterized as follows:

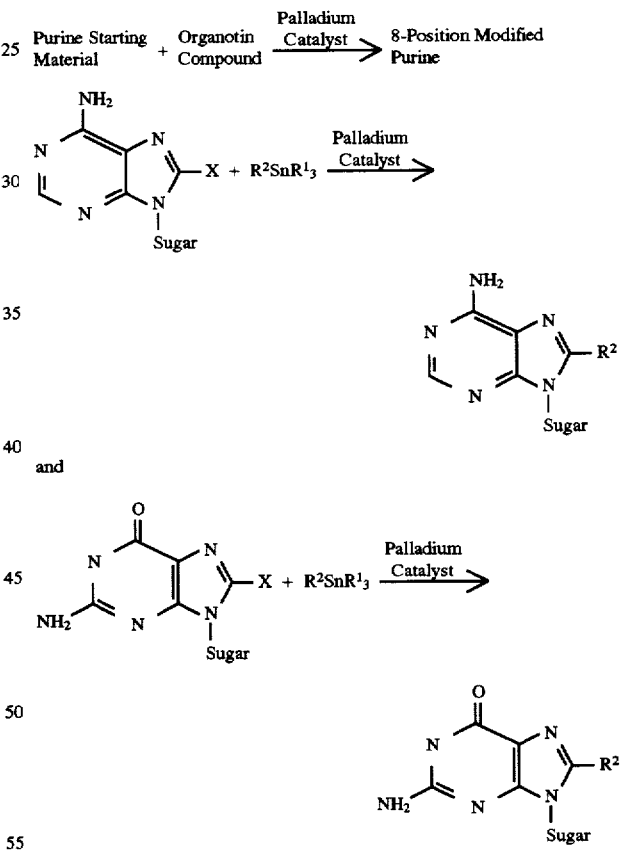

"Purine starting material" is defined herein as a purine base, purine nucleoside or purine nucleotide which is capable of being modified to include an acceptable leaving group (X). Purine starting materials include adenosine and guanosine starting materials. The leaving group can be attached to any carbon atom of the purine molecule, preferably at the 2-, 6-, or 8-position of the purine ring. The most preferred attachment is at the 8-position. The acceptable leaving group is displaced during the catalysis reaction and replaced by $R^2$ chemical moieties to yield the modified purine. The purine starting material can have a sugar moiety attached in the form of a ribose, deoxyribose, dideoxyribose, or any suitable derivatives thereof, such as a ribose or 2'-deoxyribose wherein the hydroxyl groups have been partially or fully protected.

"Acceptable leaving group" is defined herein as a group which is a suitable counterion for pallidium II, and is designated herein as X. In the most general embodiments of this invention, X is any of a number of acceptable leaving groups well known to those skilled in the art. Acceptable leaving groups include, but are not limited to, acetate, trifluoroacetate, trifluoromethyl sulfonate, tosylate, methane sulfonate and boronic esters and acids. In the preferred embodiment, X is a halogen, and in the most preferred embodiment X is bromine or iodine. The leaving group is attached to the carbon atom of the purine starting material by methods known to one of ordinary skill in the art.

"Organotin Compound" is defined herein as a tin compound which has organic groups covalently attached which can be transferred to the purine ring via palladium catalysis. In the preferred embodiments of the invention the organotin compound has the general formula of $R^2SnR^1_3$, wherein:

$R^2$ can be selected from a wide variety of chemical moieties. Specifically, $R^2$ may be any R group with a bond or atom capable of coordination to palladium and allowing for transmetallation. The bond must be connected directly to the tin or no further removed than one saturated carbon. In the preferred embodiments, $R^2$ is an C1 to C15 alkyl, C1 to C15 alkenyl, C6 to C12 aryl moiety, any of which can contain various substitutions including, but not limited to, alcohol, ether, ketone, ester, amide, amine, C1 to C15 alkane, C1 to C15 alkene, sulfide and disulfide.

$R^1$ can be any number of acceptable groups, however, preferred groups are C1 to C15 alkyl group. Particularly preferred $R^1$s are selected from the group consisting of methyl, ethyl and butyl.

In the most preferred embodiments, the organotin compound is selected from the following structures:

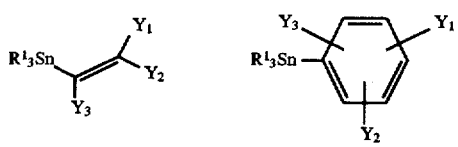

$Y_1$, $Y_2$ and $Y_3$ are independently selected from the group consisting of hydrogen, alcohols, ethers, ketones, aldehydes, esters, amides, amines, C1 to C15 alkanes, C1 to C15 alkenes, C1 to C15 alkynes, sulfides, and disulfides.

An element in the production of the modified purines is the use of a palladium catalyst. Although palladium catalyzed C-C and C-CO coupling reactions have been known for some time, a possibly erroneous proposed mechanism for the reaction has led others away from recognizing that a $PdL_3$ type catalyst would provide a more effective catalytic species that would allow for the formation of some purine analogs previously unattainable with the use of known palladium coupling catalysts. In general, the palladium catalyzed organostannane coupling reactions have utilized PdL4 catalysts. The improved $PdL_3$ catalysts of the present invention act to accelerate the formation of products that could be formed only slowly and in low yields or not at all utilizing the catalysts of the prior art.

The catalyst of the present invention may be characterized most generally as $PdL_3$, where L is one of any number of commonly employed ligands of palladium. It is within the skill and knowledge of those skilled in the art to recognize the various ligands that may be employed. Examples of common ligands (L) include, but are not limited to, $PPh_3$ (triphenyl phosphine), $(o-tol)_3P$, $CH_3CN$, DMSO, DMF,

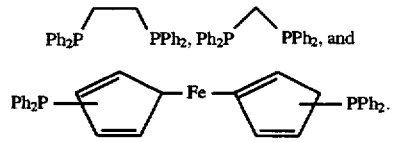

In the preferred embodiments of the catalytic species of this invention L=$PPh_3$ (triphenyl phosphine, or $P(C_6H_5)_3$). $Pd(PPh_3)_3$ is a coordinantly unsaturated species, and although not limited by theory, may exist as a dimer in solution. In coordinating solvents, such as THF, DMF, DMSO, EtOAc, acetone and dioxane, it is likely that in solution the palladium in $PdL_3$ is solvent coordinated to fill the vacancy of the metal center (18 electrons, or Pd(O) tetracoordinate).

The preparation of the preferred catalyst of the present invention is described in U.S. Ser. No. 08/076,735, filed Jun. 14, 1993, entitled "Method for Palladium Catalyzed Carbon-Carbon Coupling and Products" which is incorporated by reference herein. In the preferred embodiment, the improved catalyst composition of the present invention is a $PdL_3$ which is comprised of a solution of $Pd(OAc)_2$ and $P(C_6H_5)_3$, wherein the molar ratio of $P(C_6H_5)_3$ to $Pd(OAc)_2$ is about 3.

In the preferred embodiment the catalyst composition also includes a reducing reagent. Any suitable reducing reagent known to one of ordinary skill in the art could be included, such as triphenylphosphate, CuI, CuBr and CuCl. CuI is a preferred reducing reagent.

In the preferred embodiments of the method of this invention, the palladium catalyst is a $PdL_3$ catalyst, however, under certain circumstances other palladium catalysts, including $PdL_4$, are contemplated. In the preferred embodiments, the $PdL_3$ catalyst is prepared in THF solvent, and the reaction is run in the THF solvent. Other acceptable solvents include acetonitrile, dioxane, acetone, ethyl acetate, benzene, dimethyl formamide, dimethyl acetamide, dimethyl sulfoxide, hexamethylphosphoramide (HMPA), and hexamethylphosphoroustriamide (HMPT).

The temperature ranges for the reaction typically are between 60 and 100 degrees centrigrade, however, other suitable temperature ranges are also contemplated.

The modified purines of the present invention are contemplated for use in oligonucleotides. Standard techniques for incorporation of purine into oligonucleotides can be used with the modified purines of the invention. The oligonucleotides containing the modified purines have a number of various utilities. Specifically, the oligonucleotides interact with biological targets or have facilitating properties. They may also show antineoplastic or antiviral activity. The oligonucleotides can be useful in various diagnostic applications as well.

Stability towards endo-nucleolytic degradation in serum can be achieved by introducing 2'-deoxy-2'-fluoro- or 2'-deoxy-2'-aminonucleosides to the pyrimidine positions of the ligand (Pieken et al. (1991) Science 253:314). The 8-position modified purines of the present invention may also be coupled with 2' substituted species that would also be useful in a variety of situations. The incorporation of halogenated nucleosides may also prove valuable for enhanced ligand-target interaction.

EXAMPLES

The following examples are illustrative of preferred embodiments of methods of preparation and products of the invention and are not to be construed as limiting the invention thereto. The following general procedures were employed to produce the modified purine nucleosides described in Table I.

Materials

Tetrahydrofuran (THF) was distilled from sodium and benzophenone. Pyridine was distilled from calcium hydride. Phenyltrimethyltin, vinyltributyltin, 2-ethoxyltributyltin, 8-bromoadenosine, 8-bromoguanosine dihydrate, 2'-deoxyadenosine monohydrate were purchased from Aldrich Chemical Company. 8-Bromo-2'-deoxy-3', 5'-diacetyladenosine was prepared according to the procedure of Ikehara, M. et al.,(in Synthetic Procedure in Nucleic Acid Chemistry; Zorbach, W. W; Tipson R. S. Eds.; John Wiley and Sons, N.Y., 1968; page 189). 8-Bromo-2',3',5'-triacetyladenosine, 8-Bromo-2',3',5'-triacetylguanosine, 8-bromo-2'-deoxy-3',5'-diacetyladenosine were prepared according to the procedure of Tronchet, J. M. J., et al., (*Nucleosides & Nucleotides*, 7, 249–269, 1988).

General procedure for palladium catalyzed coupling reaction

To a reaction flask with Teflon valves was added nucleoside (0.2 mmol), organotin (0.22 mmol), Pd(OAc)$_2$ (0.01 mmol), CuI (0.03 mmol), PPh$_3$ (0.03 mmol), and THF. The flask was flushed with argon gas for 5 minutes then heated at the desired temperature until TLC indicated all nucleoside was consumed. THF was removed by vacuum and the residue was dissolved in CH$_2$Cl$_2$ (15 ml) and washed with brine (2×10 ml). After being dried over MgSO$_4$, the CH$_2$Cl$_2$ was removed and the crude product was purified by flash chromatography with 2% of MeOH in CH$_2$Cl$_2$. Proton and $^{13}$C NMR spectra were obtained in CDCl$_3$ on Bruckle ARX300 spectrometer using either Me$_4$Si or the deuterated solvent as internal standard. Fast atom bomdardment mass spectra (FAB MS) were obtained with VG 70 SE & ZAB2-EQ/FAB(+). The spectroscopic data for the coupling products follow. The various compounds made are described below and in Table I.

Compound 4: 8-Phenyl-2',3',5'-triacetyladenosine
$^1$H NMR (CDCl$_3$) δ2.02 (s, 3 H), 2.08 (s, 3 H), 2.10 (s, 3 H), 4.35 (m, 2 H), 4.52 (m, 1 H), 5.95 (d, 1 H, J=4.3 Hz), 6.02 (t, 1 H, J =5.9 Hz), 6.16 (s, 2 H), 6.50 (dd, 1 H, J=5.9, 4.3 Hz), 7.56 (m, 3 H), 7.76 (m, 2 H), 8.35 (s, 1 H); $^{13}$C NMR (CDCl$_3$) δ20.4, 20.5, 20.7, 62.9, 70.6, 72.1, 79.9, 87.8, 119.5, 128.9, 129.0, 129.6, 130.6, 150.7, 151.8, 152.6, 155.4, 169.3, 169.5, 170.7; MS (EI) m/z 469.1585 (Calc.469.1597 for C$_{22}$H$_{24}$N$_5$O$_7$).

Compound 5: 8-Vinyl-2',3',5'-triacetyladenosine
$^1$H NMR (CDCl$_3$) δ2.06 (s, 3 H), 2.07 (s, 3 H), 2.15 (s, 3 H), 4.37 (m, 2 H), 4.50 (m, 1 H), 5.75 (dd, 1 H, J =11.1, 1.2 Hz), 5.88 (t, 1 H, J=5.4 Hz), 5.95 (s, 2 H), 6.13 (d, 1 H, J=5.1 Hz), 6.25 (t, 1 H, J=5.3 Hz), 6.47 (dd, 1 H, J=17.1, 1.2 Hz), 6.87 (dd, 1 H, J=17.1, 11.1 Hz), 8.32 (s, 1 H); $^{13}$C NMR (CDCl$_3$) δ20.4, 20.6, 20.7, 63.1, 70.4, 72.4, 80.1, 86.2, 123.0, 124.8, 148.5, 150.6, 152.8, 155.1, 169.4, 169.6, 170.5, miss one carbon; MS (EI) m/z 419.1436 (Calc.419.1441 for C$_{18}$H$_{21}$N$_5$O$_7$).

Compound 6: 8-2-Ethoxyvinyl-2',3',5'-triacetyladenosine
$^1$H NMR (CDCl$_3$) δ1.44 (t, 3 H, J=7.0 Hz), 2.06 (s, 3 H), 2.09 (s, 3 H), 2.13 (s, 3 20 H), 4.01 (m, 2 H), 4.34 (m, 2 H), 4.52 (m, 1 H), 4.67 (d, 1 H, J=2.9 Hz), 5.04 (d, 1 H, J=2.9 Hz), 5.91 (s, 1 H), 6.05 (t, 1 H, J =5.8 Hz), 6.38 (dd, 1 H, J=5.8, 4.3 Hz), 6.43 (d, 1 H, J=4.3 Hz), 8.34 (s, 1 H); $^{13}$C NMR (CDCl$_3$) δ14.2, 20.4, 20.5, 20.7, 63.2, 64.2, 70.6, 72.5, 79.7, 87.7, 92.0, 119.0, 147.0, 150.5, 151.1, 153.2, 155.4, 169.2, 169.4, 170.6, miss one carbon; MS (EI) m/z 463.1691. (Calc.463.1703 for C$_{20}$H$_{25}$N$_5$O$_8$).

Compound 7: 8-Phenyl-2'-deoxy-3',5'-diacetyladenosine
$^1$H NMR (CDCl$_3$) δ2.08 (s, 3 H), 2.09 (s, 3 H), 2.06 (m, 1 H), 3.96 (m, 1 H), 4.30 (m, 1 H), 4.42 (dd, 1 H, J=11.6, 6.4 Hz), 4.59 (dd, 1 H, J=11.6, 5.3 Hz), 5.65 (m, 1 H), 5.74 (s, 2 H), 6.25 (t, 1 H, J=7.1 Hz), 7.56 (m, 3 H), 7.77 (m, 2 H), 8.35 (s, 1 H); $^{13}$C NMR (CDCl$_3$) δ20.8, 21.0, 29.7, 34.0, 63.7, 75.2, 82.6, 85.4,128.9, 129.4, 129.6, 130.4, 150.8, 151.9, 152.3, 155.3, 170.3, 170.8; MS (EI) m/z 411.1529 (Calc.411.1543 for C$_{20}$H$_{21}$N$_5$O$_5$).

Compound 8: 8-Vinyl-2'-deoxy-3',5'-diacetyladenosine
$^1$H NMR (CDCl$_3$) δ2.10 (s, 3 H), 2.14 (s, 3 H), 2.43 (m, 1 H), 3.57 (m, 1 H), 4.29 (m, 1 H), 4.38 (dd, 1 H, J=11.8, 5.2 Hz), 4.48 (dd, 1 H, J=11.1, 4.3 Hz), 5.53 (m, 1 H), 5.70 (dd, 1 H, J=11.1, 1.2 Hz), 6.28 (s, 2 H), 6.47 (m, 2 H), 6.97 (dd, 1 H, J=17.2, 11.1 Hz), 8.32 (s, 1 H); $^{13}$C NMR (CDCl$_3$) δ20.7, 20.9, 35.5, 63.6, 74.5, 82.2, 83.8, 119.3, 123.7, 124.1, 148.6, 150.6, 152.5, 155.3, 170.3, 170.5 MS (FAB) n/z (M+1)$^+$ 362.146770 (Calc. 362.146444 for C$_{16}$H$_{19}$N$_5$O$_5$+H$^+$).

Compound 9: 8-2-Ethoxyvinyl-2'-deoxy-3',5'-diacetyladenosine
$^1$H NMR (CDCl$_3$) δ1.40 (t, 3 H, J=7.0 Hz), 2.03 (s, 3 H), 2.09 (s, 3 H), 2.32 (m, 1 H), 3.71 (m, 1 H), 3.97 (m, 2 H), 4.25 (m, 1 H), 4.40 (dd, 1 H, J=17.4, 6.6 Hz), 4.55 (dd, 1 H, J=17.4, 6.6 Hz), 4.64 (d, 1 H, J=3.0 Hz), 4.95 (d, 1 H, J=3.0 Hz), 5.60 (m, 1 H), 6.06 (s, 1 H), 6.53 (t, 1 H, J =7.1 Hz), 8.27 (s, 1 H); $^{13}$C NMR (CDCl$_3$) δ14.2, 20.8, 20.9, 34.8, 63.8, 64.2, 75.0, 82.3, 85.6, 91.9, 147.3, 150.5, 151.3, 152.8, 155.6, 170.2, 170.7; MS (FAB) m/z (M+1)$^+$ 406.172659 (Calc. 406.172580 for C$_{18}$H$_{23}$N$_5$O$_6$+H$^+$).

Compound 10: 8-Phenyl-2',3',5'-triacetylguanosine
$^1$H NMR (CDCl$_3$) δ2.00 (s, 3 H), 2.06 (s, 3 H), 2.09 (s, 3 H), 4.33 (m, 2 H), 4.52 (m, 1 H), 5.88 (d, 1 H, J=3.3 Hz), 6.26 (t, 1 H, J =5.6 Hz), 6.33 (t, 1 H, J=5.3 Hz), 6.71 (s, 2 H), 7.55 (m, 3 H), 7.76 (m, 2 H), 12.46 (s, 1 H); $^{13}$C NMR (CDCl$_3$) δ20.5, 20.5, 20.7, 62.5, 70.3, 72.5, 79.1, 87.4, 117.1, 128.9, 129.2, 129.4, 129.9, 148.3, 152.2, 153.4, 159.2, 169.3, 169.4, 170.8; MS (EI) m/z 485.1546 (Calc.485.1547 for C$_{22}$H$_{23}$N$_5$O$_8$).

Compound 11: 8-Vinyl-2',3',5'-triacetylguanosine
$^1$H NMR (CDCl$_3$) δ2.04 (s, 3 H), 2.09 (s, 3 H), 2.11 (s, 3 H), 4.35 (m, 2 H), 4.46 (m, 1 H), 5.65 (d, 1 H, J=11.7 Hz), 5.97 (s, 2 H), 6.16 (s, 1 H), 6.25 (d, 1 H, J=17.1 Hz), 6.61 (s, 2 H), 6.69 (dd, 1 H, J =17.1, 5.7 Hz), 12.05 (s, 1 H); $^{13}$C NMR (CDCl$_3$) δ20.5, 20.5, 20.6, 62.8, 70.3, 72.4, 79.4, 85.9, 91.9, 116.7, 122.6, 145.5, 152.0, 153.4, 158.9, 169.4, 169.5, 170.7; MS (FAB) m/z (M+1)$^+$ 436.147290 (Calc. 436.146838 for C$_{18}$H$_{21}$N$_5$O$_8$+H$^+$).

TABLE 1

Palladium-catalyzed coupling reaction with purine nucleosides and organotin compounds

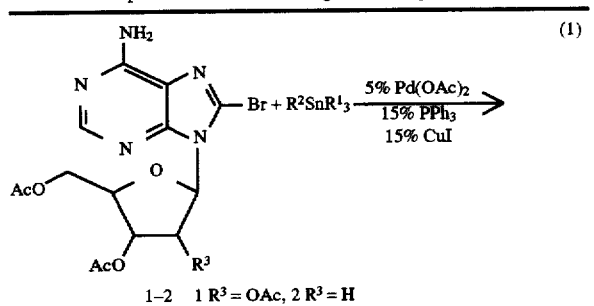

1–2  1 R$^3$ = OAc, 2 R$^3$ = H

TABLE 1-continued

Palladium-catalyzed coupling reaction with purine nucleosides and organotin compounds

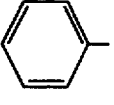

| nucleoside | R¹ | temp (°C.)/ time (h) | R² | yield (%) | product |
|---|---|---|---|---|---|
| 1 | Me | 100/24 | 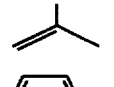 | 62 | 4 |
| 1 | Bu | 80/24<br>60/24 | 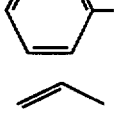 | 56<br>100 | 5 |
| 1 | Bu | 110/24<br>80/24<br>60/24 |  | 67ᵃ<br>81<br>72 | 6 |
| 2 | Me | 100/24 | 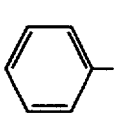 | 81 | 7 |
| 2 | Bu | 110/24<br>90/12 |  | 27<br>95 | 8 |
| 2 | Bu | 90/24 |  | 72 | 9 |
| 3 | Me | 100/48 | 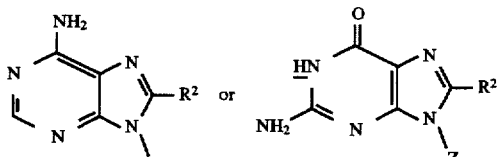 | 67 | 10 |
| 3 | Bu | 100/36<br>80/48 | 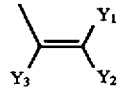 | 61<br>0 | 11 |

ᵃStarting material (5%) was recovered from the reaction.

We claim:

1. Purine nucleosides modified at the 8-position of the purine ring prepared according to a method comprising the steps of:

a) preparing a solution of a palladium catalyst of the formula $PdL_3$, wherein L is a ligand of palladium;

b) reacting a purine starting material containing a halogen leaving group attached to the 8-position of said purine starting material with an organotin compound of the formula $R^2SnR^1_3$, and $R^2$ displaces the leaving group from the purine starting material, wherein $R^1$ is a C1 to C15 alkyl, and $R^2$ is a C1 to C15 alkyl or a C1 to C15 alkenyl, in the presence of the palladium catalyst; and c) isolating and purifying said purine nucleoside.

2. A compound of the formula:

wherein $R^2$ is a C1 to C15 alkyl or a C1 to C15 alkenyl, either of which may be optionally substituted with a member of the group consisting of alcohols, ethers, ketones, esters, amides, amines, C1 to C15 alkanes, C1 to C15 alkenes, sulfides and disulfides; and Z is selected from the group consisting of a ribose, deoxyribose and dideoxyribose.

3. The compound of claim 2 wherein $R^2$ is a substituted or unsubstituted vinyl.

4. The compound of claim 3 wherein $R^2$ is

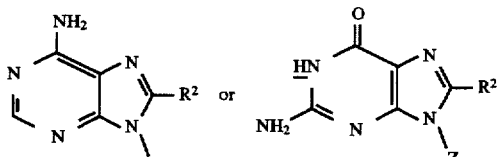

wherein $Y_1$, $Y_2$ and $Y_3$ are independently selected from the group consisting of protected alcohols, ethers, ketones, aldehydes, esters, amides, amines, C1 to C15 alkanes, C1 to C15 alkenes, C1 to C15 alkynes, and sulfides.

5. The compound of claim 2, incorporated as part of a oligonucleotide.

6. The compound of claim 5 wherein said oligonucleotide is a ribonucleic acid.

7. The compound of claim 5 wherein said oligonucleotide is a deoxyribonucleic acid.

* * * * *